United States Patent
Peng et al.

(10) Patent No.: US 10,307,082 B2
(45) Date of Patent: Jun. 4, 2019

(54) METHOD AND APPARATUS FOR HERPES ZOSTER DIAGNOSIS AND RECORDING MEDIUM USING THE METHOD

(71) Applicant: HTC Corporation, Taoyuan (TW)

(72) Inventors: De-Zhang Peng, Taoyuan (TW); Chia-Lin Mao, Taoyuan (TW); Yi-Chi Lin, Taoyuan (TW); Yih-Feng Kao, Taoyuan (TW)

(73) Assignee: HTC Corporation, Taoyuan (TW)

( * ) Notice: Subject to any disclaimer, the term of this patent is extended or adjusted under 35 U.S.C. 154(b) by 0 days.

(21) Appl. No.: 15/073,648

(22) Filed: Mar. 18, 2016

(65) Prior Publication Data

US 2016/0354013 A1    Dec. 8, 2016

Related U.S. Application Data

(60) Provisional application No. 62/169,568, filed on Jun. 2, 2015.

(51) Int. Cl.
*A61B 5/107*   (2006.01)
*A61B 5/00*    (2006.01)

(52) U.S. Cl.
CPC .......... *A61B 5/1079* (2013.01); *A61B 5/0077* (2013.01); *A61B 5/4842* (2013.01); *A61B 5/748* (2013.01); *A61B 5/7425* (2013.01)

(58) Field of Classification Search
CPC ... A61B 5/0077; A61B 5/1079; A61B 5/4842; A61B 5/7425; A61B 5/743; A61B 5/7435; A61B 5/748
See application file for complete search history.

(56) References Cited

U.S. PATENT DOCUMENTS

| | | | | |
|---|---|---|---|---|
| 2002/0182634 A1* | 12/2002 | Espy | ...................... | C12Q 1/705 435/7.1 |
| 2008/0260218 A1* | 10/2008 | Smith | .................. | A61B 5/0077 382/128 |
| 2012/0004932 A1* | 1/2012 | Sorkey | ................... | G06Q 10/06 705/3 |
| 2017/0000406 A1* | 1/2017 | Schnidar | .............. | A61B 5/1032 |

\* cited by examiner

*Primary Examiner* — Allen Porter
(74) *Attorney, Agent, or Firm* — JCIPRNET

(57) ABSTRACT

Provided are a method and an apparatus for herpes zoster diagnosis and a recording medium using the method. The method includes: displaying a body shape image that matches a body dermatome distribution for defining an affected part on the body shape image, determining an area ratio based on an area of at least one dermatome covered by the affected part, and determining whether the affected part concentrates on any one of a left side or a right side with respect to a center line of the body shape image and whether the area ratio is smaller than a predetermined ratio, so as to decide whether the defined affected part is herpes zoster.

20 Claims, 8 Drawing Sheets

METHOD AND APPARATUS FOR HERPES ZOSTER DIAGNOSIS AND RECORDING MEDIUM USING THE METHOD

CROSS-REFERENCE TO RELATED APPLICATION

This application claims the priority benefits of U.S. provisional application Ser. No. 62/169,568, filed on Jun. 2, 2015. The entirety of the above-mentioned patent application is hereby incorporated by reference herein and made a part of this specification.

BACKGROUND

Technical Field

The invention relates to a diagnosis method and a diagnosis apparatus, and more particularly, relates to a method and an apparatus for herpes zoster diagnosis.

Description of Related Art

Herpes zoster is a skin disease that is drawing more and more attention in recent years. The patient may have varicella chickenpox over areas on the skin when being infected with varicella zoster virus. After the varicella heals, the virus may still lurk in the dermatome. The virus may become active again if the body's immune system weakens. In such case, herpes may start to grow on the skin and have a strip distribution along the dermatome. Herpes mostly appear on one of the left and right sides of the body and often occur on the chest and the head and neck.

Once the virus infects the nerves, it will damage the nerves and cause severe pain. The pain may last several months or even years after the herpes heals. Therefore, early diagnosis and timely treatment of the disease is the only way to reduce or prevent the suffering. Currently, the diagnosis of herpes zoster still relies on doctors' professional judgment. It may be difficult for the general public to diagnose herpes zoster by themselves. Most people go to the doctors when they start to feel the pain, but it is usually too late for timely treatment by then. Consequently, pain is inevitable.

SUMMARY

In order for the general public to be able to diagnose herpes zoster by themselves for timely treatment, the disclosure provides a herpes zoster diagnosis method and a herpes zoster diagnosis apparatus for identifying whether a rash or a painful part drawn by the patient or identified by the apparatus matches a distribution characteristic of herpes zoster, so as to accurately diagnose herpes zoster.

The herpes zoster diagnosis method of the disclosure is adapted for an electronic apparatus. The method includes: displaying a body shape image that matches a body dermatome distribution for defining an affected part on the body shape image, determining an area ratio based on an area of at least one dermatome covered by the affected part, determining whether the affected part concentrates on any one of a left side or a right side with respect to a center line of the body shape image and whether the area ratio is smaller than a predetermined ratio, and according to a determination result, deciding whether the defined affected part is herpes zoster.

In an example of the disclosure, the method further includes acquiring body shape information of a patient to display the body shape image that matches the body shape information.

In an example of the disclosure, the step of acquiring the body shape information of the patient includes receiving medical record data or input data of the patient to obtain the body shape information, or taking a photo of a body of the patient and identifying a contour of the body of the patient in the photo to obtain the body shape information.

In an example of the disclosure, the step of defining the affected part on the body shape image includes identifying a rash part in the taken photo as the affected part.

In an example of the disclosure, the step of defining the affected part on the body shape image includes receiving a region drawn on the body shape image as the affected part.

In an example of the disclosure, the step of determining the area ratio according to the area of the at least one dermatome covered by the affected part includes determining a center dermatome that is most covered by the affected part among the at least one dermatome, setting the center dermatome and the adjacent dermatomes of the center dermatome as a target region, and calculating the area ratio of areas of the affected part outside and inside the target region.

In an example of the disclosure, the step of displaying the body shape image and defining the affected part on the body shape image includes displaying the body shape image of one of a front and a back of the body and defining the affected part on the body shape image, and the method further includes displaying the body shape image of the other one of the front and the back of the body and defining the affected part on the body shape image, determining whether the affected parts defined in the body shape images of the front and the back of the body are on the same side of the body and whether the area ratio of the areas of the affected parts, which are defined on each of the body shape images, outside and inside the corresponding target region is smaller than the predetermined ratio, and diagnosing whether the defined affected parts are herpes zoster according to the determination result.

In an example of the disclosure, the affected part includes at least one of a rash part and a painful part.

In an example of the disclosure, the step of determining whether the affected part concentrates on any one of the left side and the right side with respect to the center line of the body shape image includes determining whether an area ratio of the affected part on the left side and the right side with respect to the center line exceeds a second predetermined ratio to determine whether the affected part concentrates on any one of the left side and the right side with respect to the center line of the body shape image.

The herpes zoster diagnosis apparatus of the disclosure includes a display, a data acquisition device, a storage device, and a processor. The processor is coupled to the display, the data acquisition device, and the storage device to access and execute modules recorded in the storage device. The modules include a body shape image display module, an affected part definition module, and a diagnosis module. The body shape image display module displays a body shape image that matches a body dermatome distribution on the display. The affected part definition module defines an affected part on the body shape image by using the data acquisition device. The diagnosis module determines an area ratio according to an area of at least one dermatome covered by the affected part and determining whether the affected part concentrates on any one of a left side and a right side with respect to a center line of the body shape image and whether the calculated area ratio is smaller than a predetermined ratio to decide whether the defined affected part is herpes zoster.

In an example of the disclosure, the data acquisition device receives medical record data or input data of a patient as the body shape information of the patient for the body shape image display module to display the body shape image that matches the body shape information.

In an example of the disclosure, the data acquisition device takes a photo of a body of the patient for the body shape image display module to identify a contour of the body of the patient in the photo as the body shape information of the patient and accordingly display the body shape image that matches the body shape information. The affected part definition module identifies a rash part in the taken photo as the affected part.

In an example of the disclosure, the data acquisition device receives an input operation to draw a region on the body shape image for the affected part definition module to define the drawn region as the affected part.

In an example of the disclosure, the data acquisition device determines a center dermatome that is most covered by the affected part among the at least one dermatome, sets the center dermatome and the adjacent dermatomes of the center dermatome as a target region, and calculates the area ratio of areas of the affected part outside and inside the target region.

In an example of the disclosure, the body shape image display module respectively displays the body shape images of a front and a back of the body, and the affected part definition module respectively defines the affected part on the body shape images of the front and the back of the body, and the diagnosis module further determines whether the affected parts defined on the body shape images of the front and the back of the body are on the same side of the body and whether the area ratio of the areas of the affected parts, which are defined on each of the body shape images, outside and inside the corresponding target region is smaller than the predetermined ratio, and decides whether the defined affected parts are herpes zoster according to the determination result.

In an example of the disclosure, the affected part includes at least one of a rash part and a painful part.

In an example of the disclosure, the diagnosis module determines whether an area ratio of the affected part on the left side and the right side with respect to the center line exceeds a predetermined ratio to determine whether the affected part concentrates on any one of the left side and the right side with respect to the center line of the body shape image.

The disclosure provides a non-transitory computer readable recording medium for recording a program to be loaded by an electronic apparatus to execute the following steps: displaying a body shape image that matches a body dermatome distribution; defining an affected part on the body shape image; determining an area ratio according to an area of at least one dermatome covered by the affected part; determining whether the affected part concentrates on any one of a left side and a right side with respect to a center line of the body shape image and whether the calculated area ratio is smaller than a predetermined ratio; and deciding whether the defined affected part is herpes zoster according to a determination result.

Based on the above, in the herpes zoster diagnosis method, apparatus, and the recording medium using the method of the disclosure, the body shape image that matches the shape of the patient's body is displayed for the patient to draw the affected part on the body shape image or the apparatus automatically identifies the affected part, so as to determine whether the drawn or identified affected part is herpes zoster according to the distribution characteristic of herpes zoster. Accordingly, the patient may perform self-diagnosis of herpes zoster and continue monitoring the state of the disease.

To make the aforementioned and other features and advantages of the disclosure more comprehensible, several examples accompanied with drawings are described in detail as follows.

DESCRIPTION OF EXAMPLES

In view of the symptom that herpes zoster tends to have a strip distribution along dermatomes on a side of the body and generally does not cross a center line of the body, the disclosure provides an electronic apparatus, which displays a body shape image that matches a body dermatome distribution thereon and allows the patient to draw a rash and/or a painful part on the body shape image or automatically identifies the affected part, so as to determine whether the drawn or identified affected part is herpes zoster according to a distribution characteristic of herpes zoster. Thus, the patient is able to diagnose herpes zoster by himself/herself so as to timely receive medical treatment.

Figure 1:
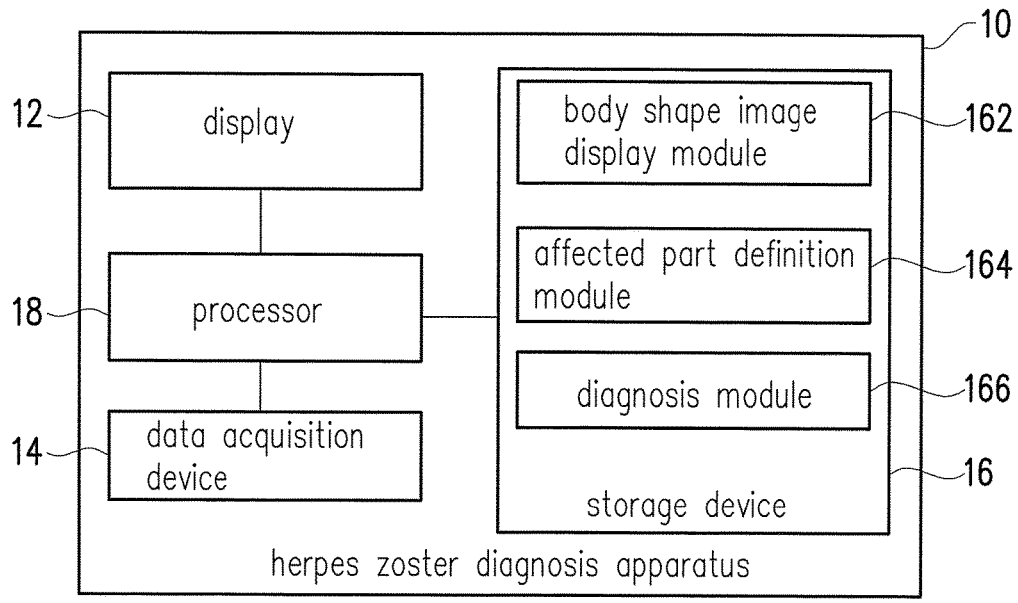
FIG. 1 is a block diagram of a herpes zoster diagnosis apparatus according to an example of the disclosure.

FIG. 1 is a block diagram of a herpes zoster diagnosis apparatus according to an example of the disclosure. Referring to FIG. 1, a herpes zoster diagnosis apparatus 10 of this example is a smart phone, a personal digital assistant (PDA), a tablet PC, a laptop, a desktop, or other types of electronic devices, for example. The herpes zoster diagnosis apparatus 10 includes a display 12, a data acquisition device 14, a storage device 16, and a processor 18 that respectively have functions as described hereinafter.

The display 12 is, for example, a liquid-crystal display (LCD), a plasma display, a vacuum fluorescent display (VFD), a light-emitting diode (LED) display, a field emission display (FED), or other suitable types of displays for displaying an image of the herpes zoster diagnosis apparatus 10.

The data acquisition device 14 is an input tool, such as a keyboard, a mouse, or a touchpad, for detecting an input operation performed by the patient and acquiring data inputted by the patient. In an example, the data acquisition device 14 may be a resistive, capacitive, optical, or any type of touch detection element, which may be integrated with the display 12 as a touch screen for detecting a touch operation performed by the patient on the display 12 and acquiring data of the touch operation. In another example, the data acquisition device 14 may be a wired or wireless communication module that supports communication protocols, such as global system for mobile communication (GSM), personal handy-phone system (PHS), code division multiple access (CDMA) system, wireless fidelity (Wi-Fi) system, or worldwide interoperability for microwave access (WiMAX) system and is capable of communicating with a remote device to acquire medical records of a patient or other relevant data. In yet another example, the data acquisition device 14 may be an image acquisition device for taking a photo of the patient's body, which may acquire image data of the patient's body by using a photosensitive element, such as a charge coupled device (CCD), or a complementary metal-oxide semiconductor (CMOS). It should be noted that the devices mentioned above are merely examples and should not be construed as limitations to the scope of the disclosure. Those skilled in the art may select one or more of the aforementioned devices to acquire the required data according to the actual requirements.

The storage device 16 may be any type of stationary or movable random access memory (RAM), read-only memory (ROM), flash memory, similar devices, or a combination of the foregoing. In this example, the storage device 16 is configured to store a body shape image and includes a display module 162, an affected part definition module 164, and a diagnosis module 166. The foregoing modules are programs stored in the storage device 16, for example.

The processor 18 is, for example, a central processing unit (CPU), a programmable microprocessor for general or special use, a digital signal processor (DSP), a programmable controller, an application specific integrated circuit (ASIC), a programmable logic device (PLD), other similar devices, or a combination of these devices. The processor 18 is connected with the display 12, the data acquisition device 14, and the storage device 16 and loads the programs of the body shape image display module 162, the affected part definition module 164, and the diagnosis module 166 from the storage device 16, so as to execute a herpes zoster diagnosis method of the disclosure. Steps of the method are described in detail in the following examples.

Figure 2:
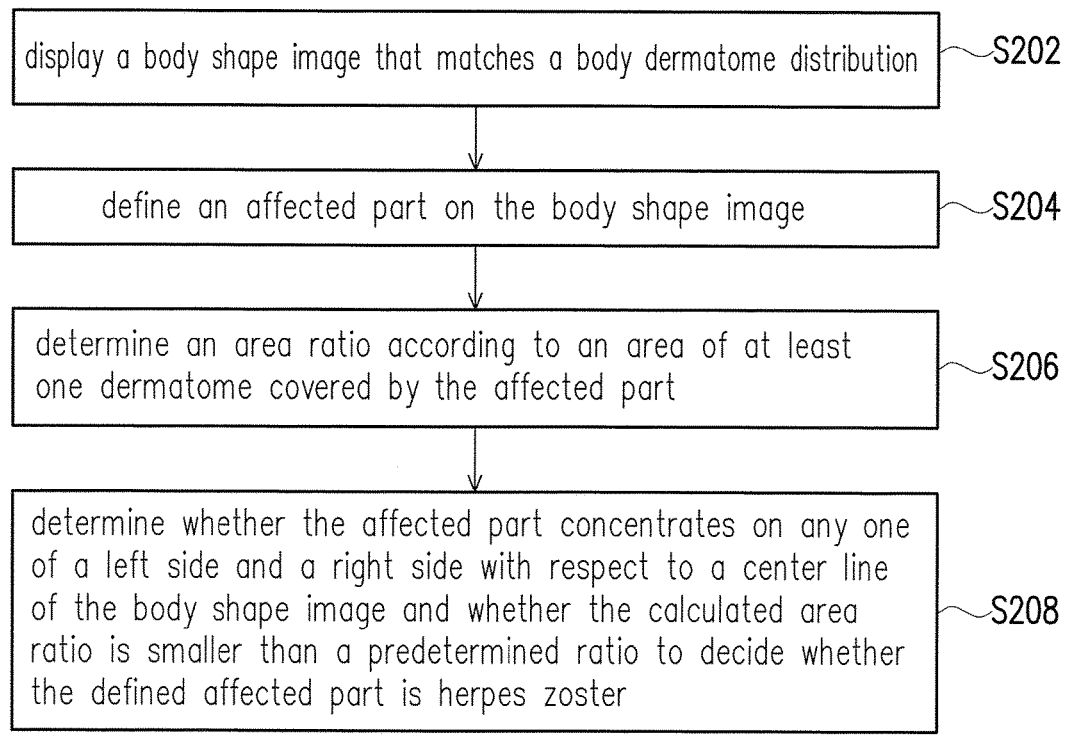
FIG. 2 is a flowchart of a herpes zoster diagnosis method according to an example of the disclosure.

FIG. 2 is a flowchart of the herpes zoster diagnosis method according to an example of the disclosure. Referring to FIG. 2, the method of this example is adapted for the herpes zoster diagnosis apparatus 10 of FIG. 1. Steps of the herpes zoster diagnosis method of the disclosure are described in detail hereinafter with reference to the components of the herpes zoster diagnosis apparatus 10.

First, the body shape image display module 162 displays a body shape image that matches a body dermatome distribution on the display 12 (Step S202). In an example, the body shape image display module 162 may display an image of a body shape of a general person on the display 12 according to statistical results of body shape information of a mass of people. In another example, the body shape image display module 162 may be connected with a remote server (e.g. a medical record database of a hospital) by the data acquisition device 14 to acquire data of medical records of the present patient, so as to obtain the body shape information of the patient. In yet another example, the body shape image display module 162 may acquire data inputted by the patient by using the data acquisition device 14 to serve as the body shape information of the patient, and accordingly display the body shape image that matches the body shape information on the display 12. For example, the body shape image display module 162 collects questions that a doctor may ask the patient for diagnosis of herpes zoster in advance and acquires the body shape information, such as height, weight, and measurements, of the patient through inquiry (e.g. displays the questions on a screen or plays audio questions), so as to obtain the body shape information of the patient from the patient's reply and display the body shape image that matches the body shape information on the display 12.

Then, the affected part definition module 164 defines an affected part on the body shape image by using the data acquisition device 14 (Step S204). In an example, the affected part definition module 164 may receive an input operation of the patient by using the data acquisition device 14 to draw a region on the body shape image and define the region drawn by the patient as the affected part.

Figure 3A:
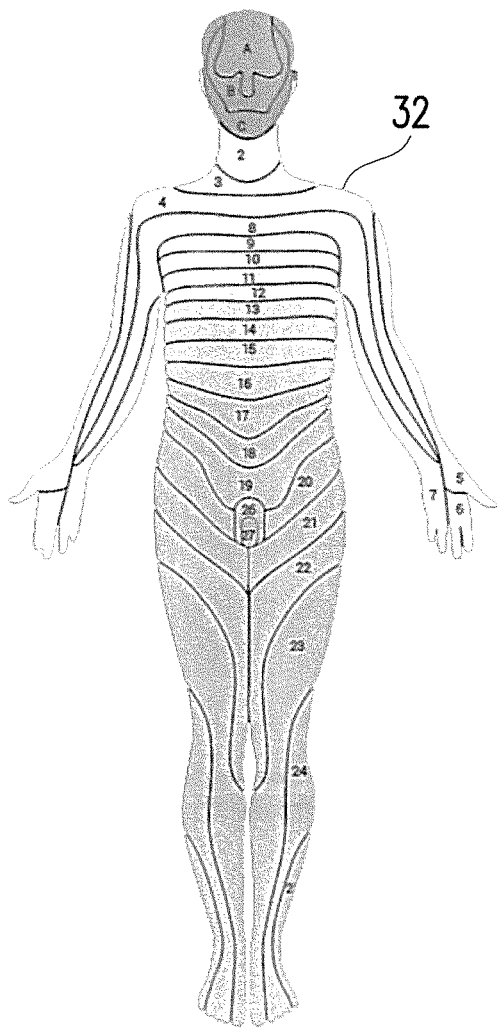
FIG. 3A and FIG. 3B are figures respectively showing a body dermatome distribution according to an example of the disclosure.
Figure 3B:
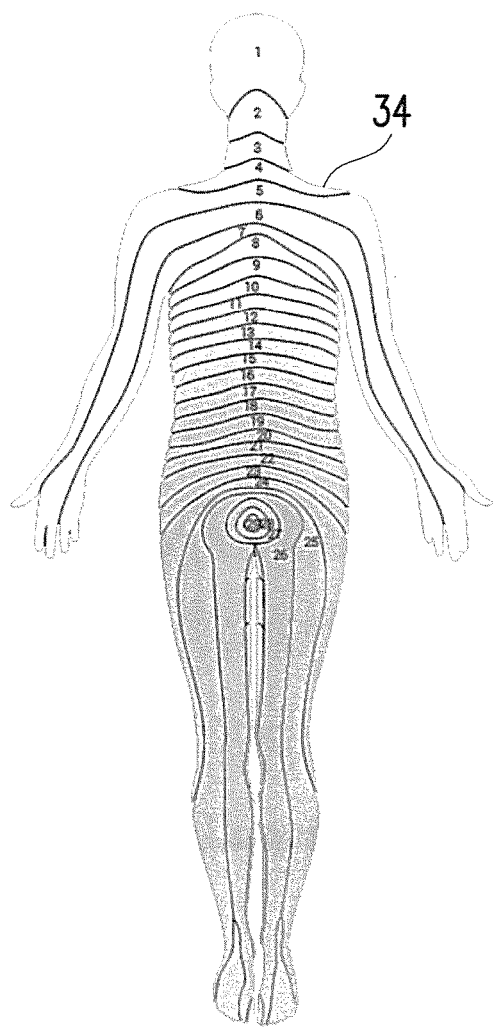
Figure 4A:
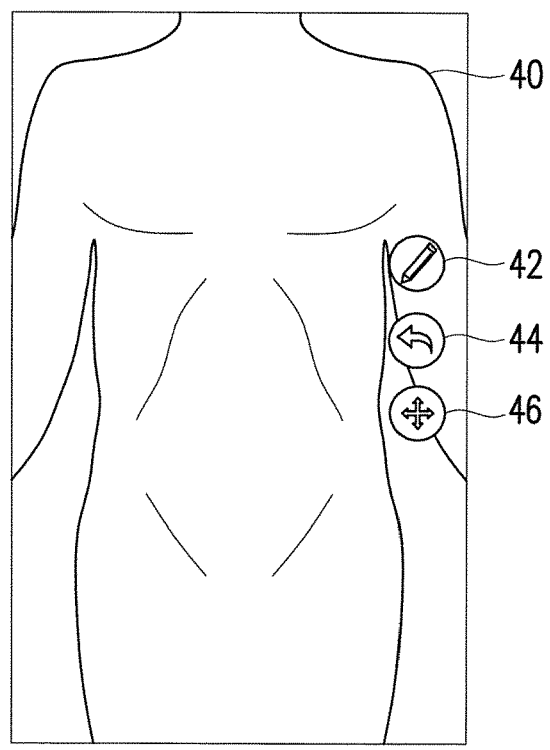
FIG. 4A and FIG. 4B show an example of defining an affected part on a body shape image according to an example of the disclosure.
Figure 4B:
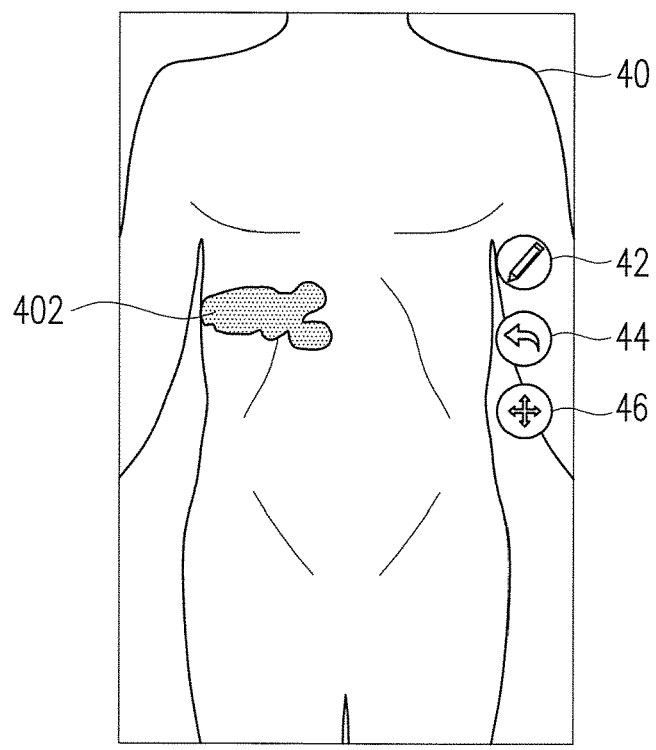

For example, FIG. 3A and FIG. 3B are figures respectively showing a body dermatome distribution according to an example of the disclosure. FIG. 4A and FIG. 4B show an example of defining the affected part on the body shape image according to an example of the disclosure. Specifically, FIG. 3A illustrates a dermatome distribution 32 of the front of the body and FIG. 3B illustrates a dermatome distribution 34 of the back of the body. The regions in FIG. 3A and FIG. 3B respectively represent different dermatomes, and the numbers labelled therein represent the number of the dermatome. FIG. 4A illustrates a body shape image 40 of the front of the patient's body. The body shape image 40 matches the dermatome distribution of the front of the body as illustrated in FIG. 3A, for example. In this example, the body shape image 40 is displayed on an electronic apparatus to provide a drawing tool 42, an undoing tool 44, and a moving tool 46 for the patient to draw the affected part. Thereby, the patient may select the drawing tool 42 to draw an affected part 402 (as shown in FIG. 4B) on the body shape image 40 in accordance with where the rash is located on the body. Because the body shape image 40 matches the dermatome distribution 32, the electronic apparatus compares the body shape image 40 with the dermatome distribution 32 to determine the relative position of the affected part 402 on the body shape image 40 so as to determine the corresponding dermatome in the dermatome distribution 32.

Reverting to the flowchart of FIG. 2, after defining the affected part, the diagnosis module 166 calculates an area of each dermatome covered by the affected part according to the regions covered by the affected part and, among the dermatomes, determines a center dermatome that is most covered by the affected part, and then sets the center dermatome and the dermatomes adjacent thereto as a target region to calculate an area ratio of an area of the affected part outside the target region to an area of the affected part inside the target region. That is, the diagnosis module 166 divides the area of the affected part outside the target region by the area of the affected part inside the target region to obtain the area ratio (Step S206).

Last, the diagnosis module 166 determines whether the affected part concentrates on any one of a left side and a right side with respect to a center line of the body shape image and whether the calculated area ratio is smaller than a predetermined ratio, so as to decide whether the defined affected part is herpes zoster (Step S208). The predetermined ratio ranges from 0.1 to 0.3, and preferably 0.2, for example, but not limited thereto. The diagnosis module 166 determines that the defined affected part is herpes zoster if the above two conditions are both met (that is, the affected part concentrates on any one of the left side and the right side with respect to the center line of the body shape image and the area ratio is smaller than the predetermined ratio). It should be noted that, in another example, the diagnosis module 166 may divide the area of the affected part inside the target region by the area of the affected part outside the target region to obtain the area ratio and determine whether the area ratio exceeds another predetermined ratio, as a condition for determining whether the affected part is herpes zoster.

Specifically, the affected part may have two kinds of distributions. That is, the affected part may only appear on the left side or the right side with respect to the center line of the body shape image or appear on both the left side and the right side across the center line. If the affected part appears on only one side, the condition that the affected part concentrates on any one of the left side and the right side with respect to the center line of the body shape image is met; however, if the affected part appears on both the left side and the right side, the diagnosis module 166 may further determine whether a ratio of the areas of the affected part on two sides of the center line exceeds the predetermined ratio, so as to determine whether the condition that the affected part concentrates on any one of the left side and the right side with respect to the center line of the body shape image is met. Specifically, the diagnosis module 166 respectively calculates the areas covered by the affected part on the left side and the right side of the center line and divides the area having a smaller value by the area having a greater value to obtain the area ratio. If the area ratio is smaller than the predetermined ratio (i.e. 0.1-0.3, and preferably 0.2, but not limited thereto), the diagnosis module 166 determines that the affected part concentrates on the left side or the right side with respect to the center line of the body shape image, and the characteristic of the affected part matches a symptom of herpes zoster. It should be noted that, in another example, the diagnosis module 166 may divide the area having the greater value by the area having the smaller value to obtain the area ratio and determine whether the area ratio exceeds another predetermined ratio, so as to determine whether the affected part concentrates on any one of the left side and the right side with respect to the center line of the body shape image.

In addition, after the diagnosis module 166 determines that the affected part concentrates on the left side or the right side with respect to the center line of the body shape image, the diagnosis module 166 sets the dermatome that is most covered by the affected part as the center dermatome and uses the center dermatome and all the dermatomes adjacent thereto (the number of the dermatomes adjacent to the center dermatome may vary depending on the position of the center dermatome) as the target region to determine whether the area ratio of the areas of the affected part outside and inside the target region exceeds the predetermined ratio and thereby decide whether the defined affected part is herpes zoster.

Figure 5:
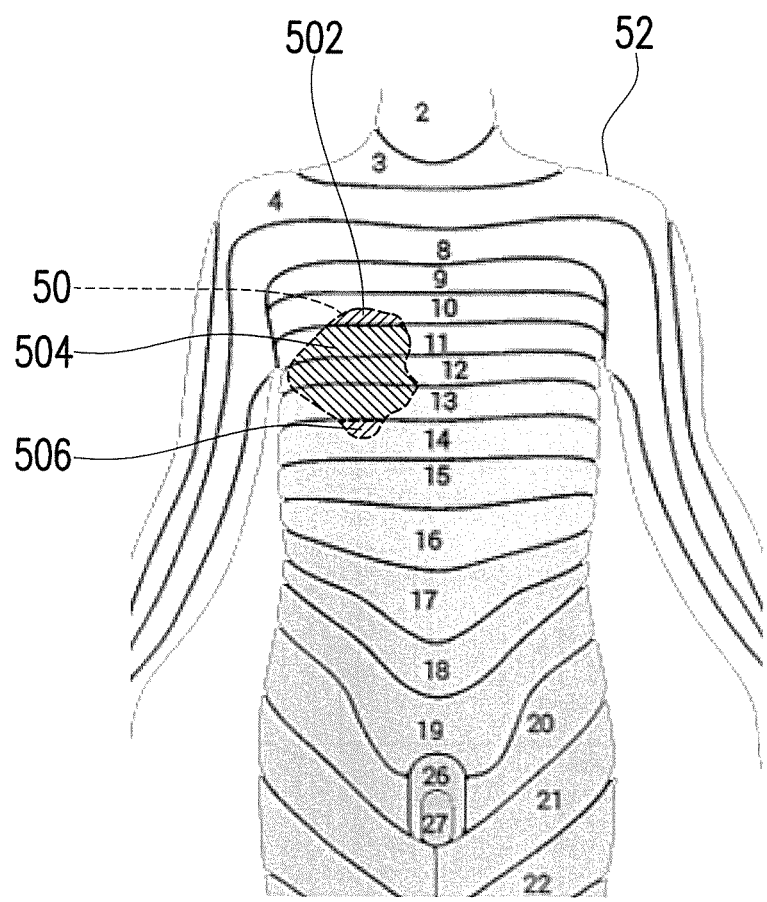
FIG. 5 shows an example of determining the number of dermatomes covered by the affected part according to an example of the disclosure.

For example, FIG. 5 shows an example of determining the number of the dermatomes covered by the affected part according to an example of the disclosure. Referring to FIG. 5, in this example, an affected part 50 drawn by the patient is mapped to a dermatome distribution 52 of the body for describing detailed steps of determining the number of the dermatomes covered by the affected part according to this example. The affected part 50 covers dermatomes respectively numbered as 10, 11, 12, 13, and 14 in the dermatome distribution 52. The diagnosis module 166 respectively calculates the areas of the five dermatomes covered by the affected part 50 and determines the dermatome 12 that is most covered by the affected part 50 as the center dermatome, and then sets the center dermatome and the adjacent dermatomes 11 and 13 as a target region 504. Last, the diagnosis module 166 calculates the area ratio of the area of the affected part 50 outside the target region 504 (i.e. a total of the areas of regions 502 and 506) to the area of the affected part 50 inside the target region 504 and determines whether the area ratio is smaller than the predetermined ratio (e.g. 0.2), and thereby decides whether the affected part 50 is herpes zoster. If the area ratio does not exceed the predetermined ratio and the affected part concentrates on any one of the left side and the right side with respect to the center line of the body shape image, the diagnosis module 166 determines that the defined affected part 50 is herpes zoster.

By the method described above, the patient only needs to draw the affected part on the body shape image displayed by the electronic apparatus and then the electronic apparatus will automatically diagnose whether the affected part is herpes zoster. Thus, the electronic apparatus of the disclosure may serve as a self-diagnosis tool that allows the patient to diagnose herpes zoster by himself/herself so as to discover the symptom earlier and timely make treatment.

It should be noted that, in another example, the electronic apparatus of the disclosure may further identify the shape of the patient's body and the region where the affected part is located by taking a photo of the patient's naked body, so as to automatically diagnose whether the identified affected part is herpes zoster. Another example is described in detail below.

Figure 6:
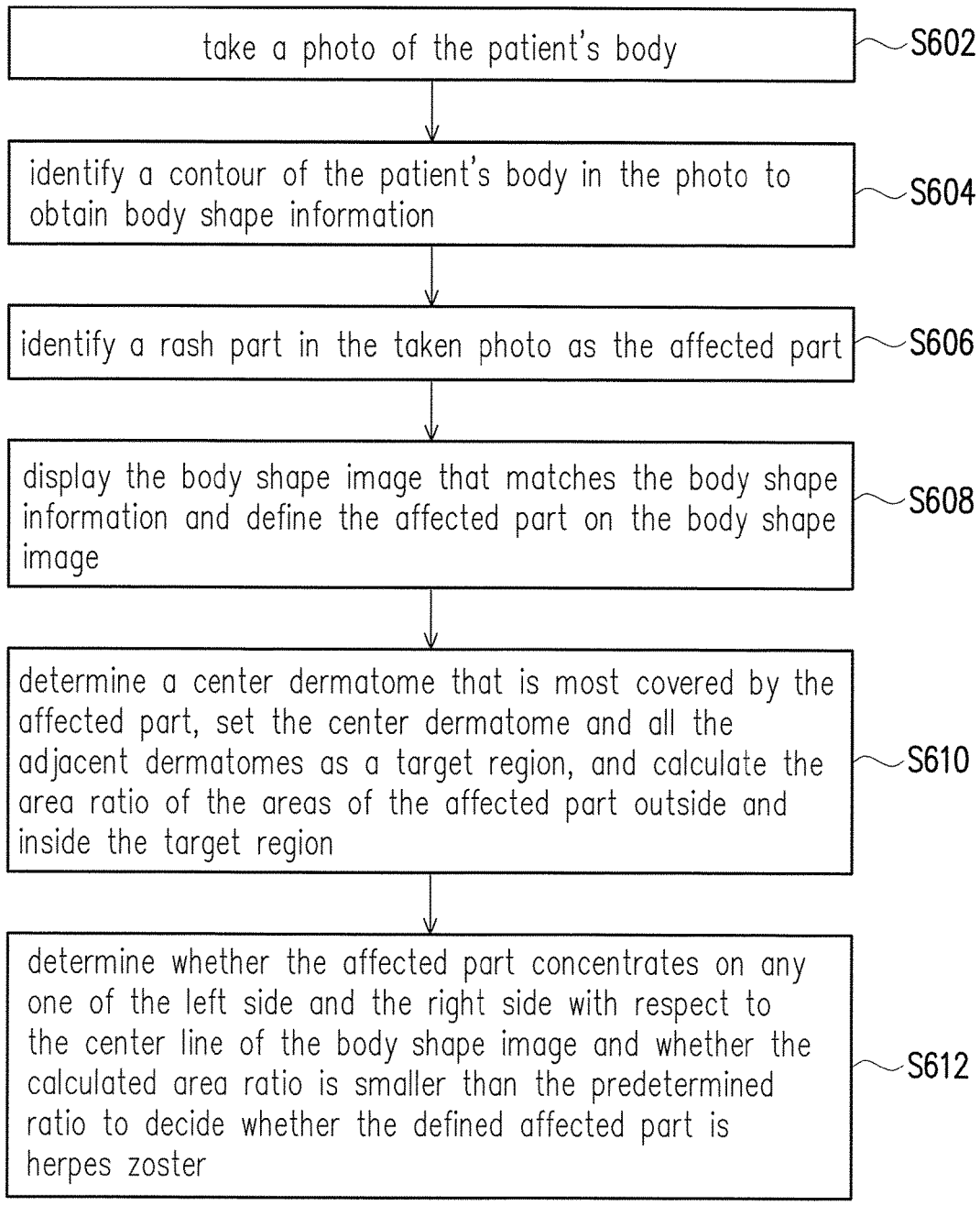
FIG. 6 is a flowchart of a herpes zoster diagnosis method according to an example of the disclosure.

FIG. 6 is a flowchart of a herpes zoster diagnosis method according to an example of the disclosure. Referring to FIG. 6, the method of this example is adapted for the herpes zoster diagnosis apparatus 10 of FIG. 1. Steps of the herpes zoster diagnosis method of the disclosure are described in detail hereinafter with reference to the components of the herpes zoster diagnosis apparatus 10.

First, the patient uses the data acquisition device 14 (e.g. a camera) of the electronic apparatus 10 to take a photo of the patient's body (Step S602). Then, the body shape image display module 162 automatically identifies a contour of the patient's body in the photo to serve as body shape information of the patient (Step S604). The body shape image display module 162 identifies the contour of the patient's body in the photo by an edge detection technique, for example, so as to determine the shape of the patient's body according to the range covered by the contour.

Further, the affected part definition module 164 identifies a rash part in the photo as the affected part (Step S606). Because the skin where the rash is located may have a darker color or have a specific pattern (which may vary depending on the rash type) as compared with the normal skin, the affected part definition module 164 further identifies the rash part on the patient's body by using an image processing method, such as feature identification.

Thereafter, the body shape image display module 162 displays the body shape image that matches the identified body shape information on the display 12 and the affected part definition module 164 defines the affected part on the body shape image (Step S608).

After the affected part is defined, the diagnosis module 166 calculates the area of each dermatome covered by the affected part according to the regions covered by the affected part and, among the dermatomes, determines the center dermatome that is most covered by the affected part, and then uses the center dermatome and all the dermatomes adjacent thereto as the target region to calculate the area ratio of the areas of the affected part outside and inside the target region (Step S610). Last, the diagnosis module 166 determines whether the affected part concentrates on any one of the left side and the right side with respect to the center line of the body shape image and whether the calculated area ratio is smaller than the predetermined ratio, so as to decide whether the defined affected part is herpes zoster (Step S612). Steps S610 and S612 described above are the same as or similar to Steps S206 and S208 of the above example. Thus, details thereof are not repeated hereinafter.

By the method described above, the patient only needs to take a photo of his/her naked body with use of the electronic apparatus and accordingly the electronic apparatus will automatically identify the body shape and the affected part to diagnose whether the affected part is herpes zoster. Accordingly, the complicated setting and drawing processes are omitted.

In the above example, the electronic apparatus displays the body shape image of only one side of the body and the affected part is drawn only on this body shape image for diagnosis of herpes zoster. In yet another example, however, the electronic apparatus may display body shape images of a front and a back of the body for the patient to draw the affected part on these body shape images, such that the body shape images of the front and the back of the body are checked in combination for diagnosing herpes zoster, so as to increase the accuracy of diagnosis. Another example is described in detail below.

Figure 7:
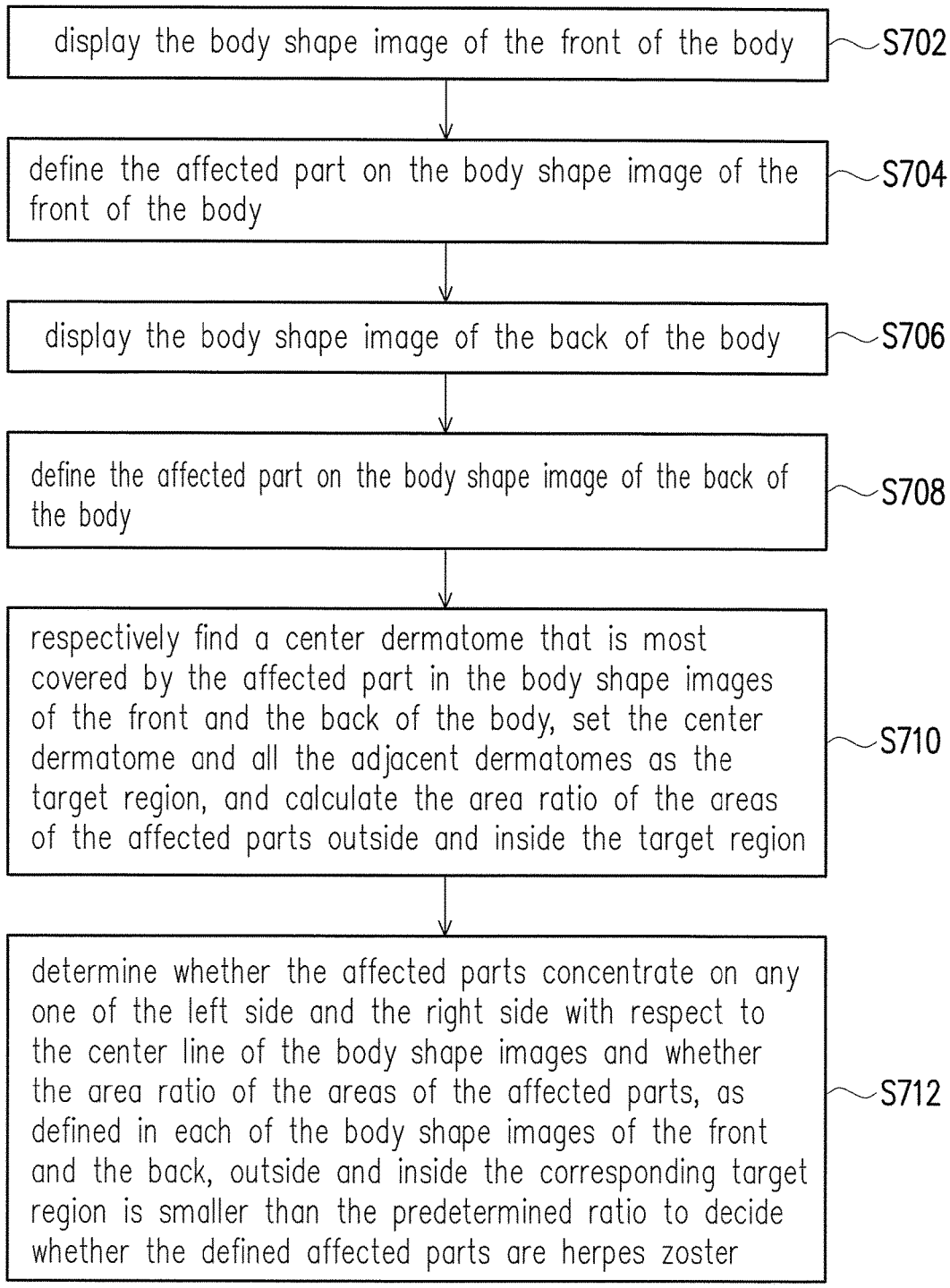
FIG. 7 is a flowchart of a herpes zoster diagnosis method according to an example of the disclosure.

FIG. 7 is a flowchart of a herpes zoster diagnosis method according to an example of the disclosure. Referring to FIG. 7, the method of this example is adapted for the herpes zoster diagnosis apparatus 10 of FIG. 1. Steps of the herpes zoster diagnosis method of the disclosure are described in detail hereinafter with reference to the components of the herpes zoster diagnosis apparatus 10.

First, the body shape image display module 162 displays the body shape image of the front of the body on the display 12 (Step S702), wherein the body shape image matches a dermatome distribution of the front of the body, for example. Then, the affected part definition module 164 defines the affected part on the body shape image of the front of the body by using the data acquisition device 14 (Step S704). Steps S702 and S704 described above are the same as or similar to Steps S202 and S204 of the above example. Thus, details thereof are not repeated hereinafter.

Different from the above example, after the affected part of the front of the body is defined, the body shape image display module 162 further displays a body shape image of the back of the body on the display 12 (Step S706), and this body shape image matches a dermatome distribution of the back of the body. Then, the affected part definition module 164 defines the affected part on the body shape image of the back of the body by using the data acquisition device 14 (Step S708). Methods of displaying the body shape image of the back of the body and defining the affected part thereon are the same as or similar to the methods of displaying the body shape image of the front of the body and defining the affected part thereon as described in the above example. Thus, details thereof are not repeated hereinafter.

After the affected parts on the front and the back of the body is defined, the diagnosis module 166 respectively calculates the area of each dermatome covered by the affected part according to the regions covered by the affected part in the body shape images of the front and the back of the body and determines a center dermatome that is most covered by the affected part among the dermatomes, and then sets the center dermatome and all the dermatomes adjacent thereto as the target region to calculate the area ratio of the areas of the affected parts located outside and inside the target region (Step S710).

Last, the diagnosis module 166 checks the body shape images of the front and the back of the body in combination to determine whether the affected parts defined in the body shape images are on the same side (i.e. the left side or the right side) of the body and whether the area ratio of the areas of the affected parts, as defined in each of the body shape images of the front and the back, outside and inside the corresponding target region is smaller than the predetermined ratio, so as to decide whether the defined affected parts are herpes zoster (Step S712). To be specific, since the dermatomes are connected along regions of the skin and are distributed on the front and the back of the body, the range of herpes zoster may not be limited to only the front or the back of the body and may occur on both the front and the back of the body simultaneously, but the herpes zoster still concentrates on one of the left side and the right side of the body. Accordingly, the diagnosis module 166 checks whether the affected parts shown on the body shape images of the front and the back of the patient's body are on the same side of the body, so as to more accurately diagnose herpes zoster.

Figure 8A:
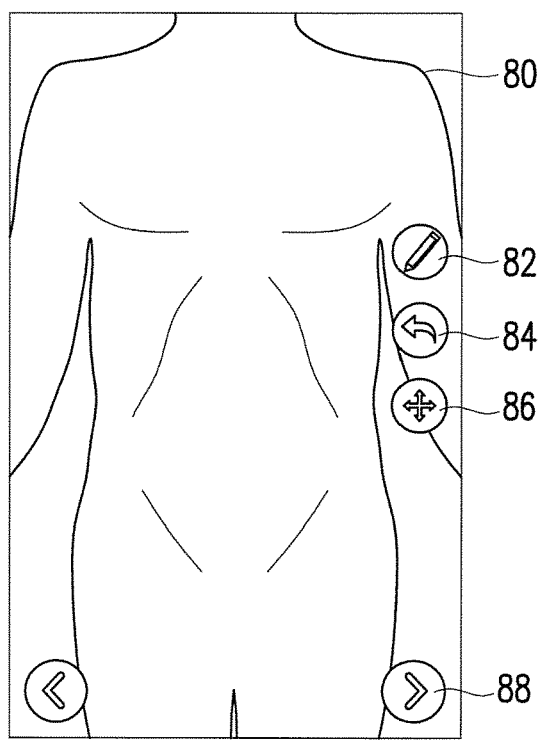
FIG. 8A to FIG. 8D show an example of defining the affected part on the body shape image according to an example of the disclosure.
Figure 8B:
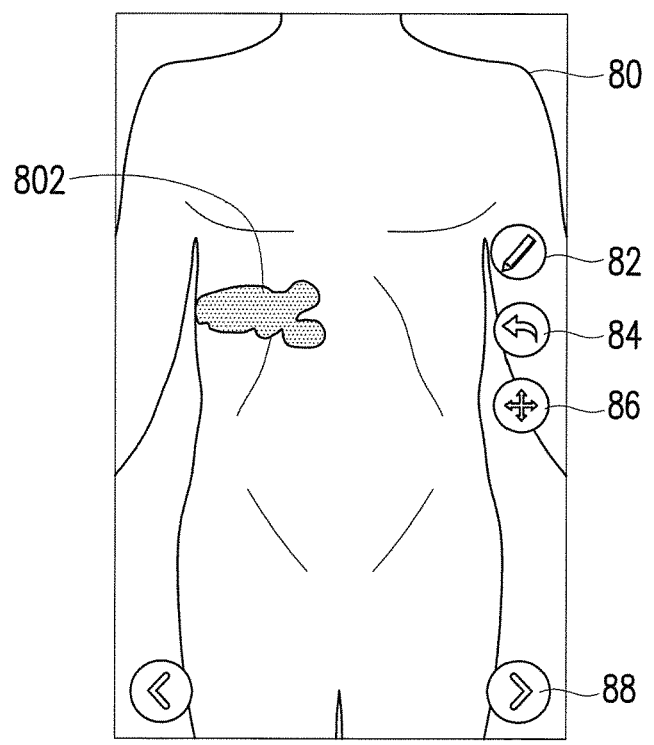
Figure 8C:
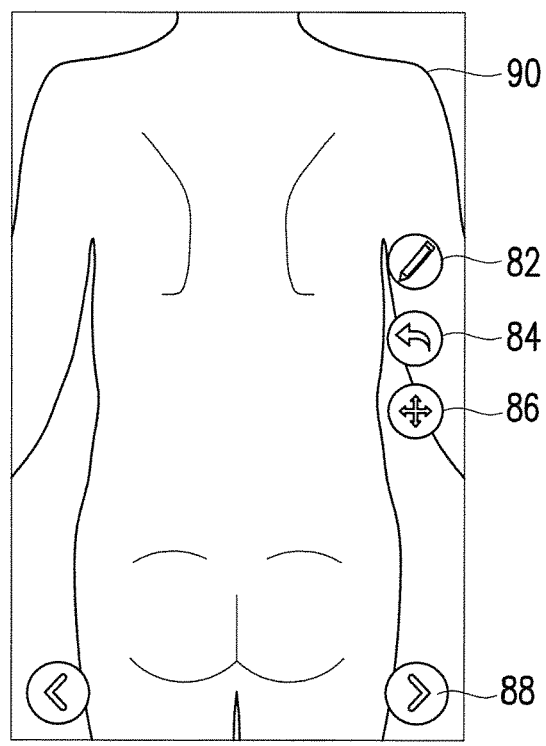
Figure 8D:
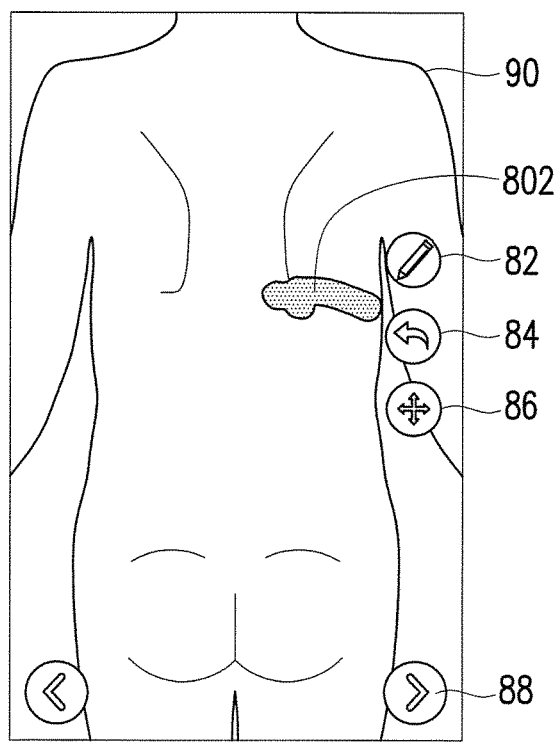

For example, FIG. 8A to FIG. 8D show an example of defining the affected part on the body shape image according to an example of the disclosure. FIG. 8A illustrates a body shape image 80 of the front of the patient's body. The body shape image 80 matches the dermatome distribution 32 of the front of the body as illustrated in FIG. 3A, for example. In this example, the body shape image 80 is displayed on an electronic apparatus with a drawing tool 82, an undoing tool 84, and a moving tool 86 for the patient to draw the affected part. Thereby, the patient may select the drawing tool 82 to draw an affected part 802 on the body shape image 80 in accordance with where the rash is on the body. Then, the patient may select a switching tool 88 to switch to a body shape image 90 of the back of the body. The body shape image 90 matches the dermatome distribution 34 of the back of the body as illustrated in FIG. 3B, for example. Likewise, the patient may select the drawing tool 82 to draw an affected part 902 on the body shape image 90 in accordance with where the rash is on the body. After the patient completes the drawing, the electronic apparatus checks the body shape image 80 and the body shape image 90 in combination to determine whether the defined affected part 802 and affected part 902 are on the same side of the body. Because the affected part 802 and the affected part 902 are both on the right side of the body, the electronic apparatus determines that the affected part 802 and the affected part 902 form herpes zoster.

It should be noted that, in addition to appearing on the same side on the front and the back of the body, herpes zoster may cover the same dermatome. Accordingly, in another example, when checking the body shape images of the front and the back of the body in combination, in addition to determining whether the affected parts defined in the body shape images are on the same side of the body, the diagnosis module 166 further determines whether the area ratio of the areas of the affected parts, as defined in each of the body shape images, outside and inside the corresponding target region (i.e. the center dermatome and all the adjacent dermatomes defined in the above example) is smaller than the predetermined ratio, so as to diagnose whether defined affected parts are herpes zoster. If the affected parts on the front and the back of the body are on the same side and cover the same dermatome, the diagnosis module 166 further confirms that the affected parts are herpes zoster. Thus, the accuracy of the electronic apparatus of the disclosure in diagnosis of herpes zoster is enhanced.

Moreover, herpes zoster does not necessarily cause rash on the body skin, and patients who have stronger immunity may feel pain only (i.e. neuropathic pain resulting from damage of dermatomes). Therefore, in yet another example, the affected part definition module 164 of the disclosure may define a rash part or a painful part on the body shape image displayed by the body shape image display module 162 and the diagnosis module 166 determines whether the defined rash part or painful part concentrates on any one of the left side and the right side with respect to the center line of the body shape image and whether the area ratio of the areas of the rash part or the painful part outside and inside the corresponding target region (i.e. the center dermatome and the adjacent dermatomes defined in the above example) is smaller than the predetermined ratio, so as to decide whether the defined affected part is herpes zoster. By cross-comparison between the rash part and the painful part, the accuracy of the electronic apparatus of the disclosure in diagnosis of herpes zoster is further enhanced.

The disclosure further provides a non-transitory computer readable recording medium that records a computer program therein. The computer program is for executing the steps of the herpes zoster diagnosis method described above and is composed of a plurality of program code snippets (e.g. organization diagram building program code snippet, list approval program code snippet, setting program code snippet, and deployment program code snippet). Moreover, after the program code snippets are loaded to the electronic apparatus and executed, the steps of the herpes zoster diagnosis method are accomplished.

To conclude the above, in the herpes zoster diagnosis method, apparatus, and the recording medium using the method of the disclosure, the body shape image of the patient is displayed on the electronic apparatus for the patient to manually draw the affected part or the apparatus automatically identifies the affected part, so as to define the affected part of herpes zoster on the body shape image. According to the disclosure, whether the defined affected part is herpes zoster can be determined accurately based on the distribution characteristic of herpes zoster. Thus, the electronic apparatus of the disclosure allows the patient to diagnose herpes zoster by himself/herself through a simple operation and continue monitoring the progress of recovery after receiving medical treatment, which is an additional function of the electronic apparatus.

It will be apparent to those skilled in the art that various modifications and variations can be made to the disclosed examples without departing from the scope or spirit of the disclosure. In view of the foregoing, it is intended that the disclosure covers modifications and variations of this disclosure provided that they fall within the scope of the following claims and their equivalents.

What is claimed is:

1. A method for diagnosing herpes zoster, wherein the steps of diagnosing are performed with an electronic apparatus having a processor, a display and a data acquisition device, comprising:
    displaying, by the processor on the display, a body shape image that matches a body dermatome distribution in response to the body shape image provided via the data acquisition device per a user request;
    defining, by the processor, an affected part on the body shape image using the data acquisition device;
    determining, by the processor, a first area ratio according to an area of at least one dermatome covered by the affected part, wherein the determining comprises:
        determining a center dermatome that is most covered by the affected part among the at least one dermatome;
        setting the center dermatome and dermatomes of the body dermatome distribution that are adjacent to the center dermatome as a target region;
        calculating an area of the center dermatome and the adjacent dermatomes;
        calculating an area of dermatomes of the body dermatome distribution that are outside of the target region; and
        calculating the first area ratio as a ratio of the area of the center dermatome and the adjacent dermatomes to the area of the dermatomes that are outside of the target region;
    determining, by the processor, whether the affected part concentrates on any one of a left side and a right side with respect to a center line of the body shape image and whether the first area ratio is smaller than a first predetermined ratio, wherein the first predetermined ratio is between 0.1 and 0.3;
    deciding, by the processor, whether the defined affected part is herpes zoster according to a determination result; and
    treating the affected part in response to the defined affected part being decided to be the herpes zoster according to the determination results.

2. The method according to claim 1, further comprising:
    acquiring body shape information of a patient to display the body shape image that matches the body shape information.

3. The method according to claim 2, wherein the step of acquiring the body shape information of the patient comprises receiving medical record data or input data of the patient to obtain the body shape information, or taking a photo of a body of the patient and identifying a contour of the body of the patient in the photo by an edge detection technique to obtain the body shape information.

4. The method according to claim 1, wherein the step of defining the affected part on the body shape image comprises:
    identifying a rash part in a taken photo as the affected part.

5. The method according to claim 1, wherein the step of defining the affected part on the body shape image comprises:
    receiving a region drawn on the body shape image as the affected part.

6. The method according to claim 1, wherein the step of displaying the body shape image and defining the affected part on the body shape image comprises displaying the body shape image of one of a front and a back of the body and defining the affected part on the body shape image, and the herpes zoster diagnosis method further comprises:
    displaying the body shape image of the other one of the front and the back of the body and defining the affected part on the body shape image;
    determining whether the affected parts defined in the body shape images of the front and the back of the body are on the same side of the body and whether the first area ratio of the areas of the affected parts, which are defined on each of the body shape images, outside and inside the corresponding target region is smaller than the first predetermined ratio; and diagnosing whether the defined affected parts are herpes zoster according to the determination result.

7. The method according to claim 1, wherein the affected part comprises at least one of a rash part and a painful part.

8. The method according to claim 1, wherein the step of determining whether the affected part concentrates on any one of the left side and the right side with respect to the center line of the body shape image comprises:
determining whether a second area ratio of the affected part on the left side and the right side with respect to the center line exceeds a second predetermined ratio to determine whether the affected part concentrates on any one of the left side and the right side with respect to the center line of the body shape image.

9. The method according to claim 8, wherein the second predetermined ratio is between 0.1 and 0.3.

10. The method according to claim 1, wherein the first predetermined ratio is 0.2.

11. A herpes zoster diagnosis apparatus, comprising:
a display;
a data acquisition device;
a storage device recording program instructions; and
a processor coupled to the display and the storage device and configured to execute program instructions to:
display a body shape image that matches a body dermatome distribution on the display in response to the body shape image provided via the data acquisition device per a user request;
define an affected part on the body shape image by using the data acquisition device;
determine a first area ratio according to an area of at least one dermatome covered by the affected part, wherein the program instruction to determine the first area ratio according to the area of the at least one dermatome covered by the affected part comprises further program instructions to:
determine a center dermatome that is most covered by the affected part among the at least one dermatome;
set the center dermatome and dermatomes of the body dermatome distribution that are adjacent to the center dermatome as a target region;
calculate an area of the center dermatome and the adjacent dermatomes;
calculate an area of dermatomes of the body dermatome distribution that are outside of the target region; and
calculate the first area ratio as a ratio of the area of the center dermatome and the adjacent dermatomes to the area of the dermatomes that are outside of the target region;
determine whether the affected part concentrates on any one of a left side and a right side with respect to a center line of the body shape image and whether the calculated first area ratio is smaller than a first predetermined ratio to decide whether the defined affected part is herpes zoster, wherein the first predetermined ratio is between 0.1 and 0.3; and
treat the affected part in response to the defined affected part being decided to be the herpes zoster according to the determination results.

12. The herpes zoster diagnosis apparatus according to claim 11, wherein the data acquisition device receives medical record data or input data of a patient as body shape information of the patient for the processor to display the body shape image that matches the body shape information.

13. The herpes zoster diagnosis apparatus according to claim 11, wherein the data acquisition device takes a photo of a body of the patient for the processor to identify a contour of the body of the patient in the photo as the body shape information of the patient and accordingly display the body shape image that matches the body shape information, wherein the processor identifies a rash part in the taken photo as the affected part.

14. The herpes zoster diagnosis apparatus according to claim 11, wherein the data acquisition device receives an input operation to draw a region on the body shape image for the processor to define the drawn region as the affected part.

15. The herpes zoster diagnosis apparatus according to claim 11, wherein the processor is further configured to:
respectively display the body shape images of a front and a back of the body;
respectively define the affected part on the body shape images of the front and the back of the body; and
determine whether the affected parts defined on the body shape images of the front and the back of the body are on the same side of the body and whether the first area ratio of the areas of the affected parts, which are defined on each of the body shape images, outside and inside the corresponding target region is smaller than the first predetermined ratio, and decide whether the defined affected parts are herpes zoster according to the determination result.

16. The herpes zoster diagnosis apparatus according to claim 10, wherein the affected part comprises at least one of a rash part and a painful part.

17. The herpes zoster diagnosis apparatus according to claim 10, wherein the processor determines whether a second area ratio of the affected part on the left side and the right side with respect to the center line exceeds a second predetermined ratio to determine whether the affected part concentrates on any one of the left side and the right side with respect to the center line of the body shape image.

18. The herpes zoster diagnosis apparatus according to claim 17, wherein the second predetermined ratio is between 0.1 and 0.3.

19. The herpes zoster diagnosis apparatus according to claim 11, wherein the first predetermined ratio is 0.2.

20. A non-transitory computer readable recording medium that records a program loaded by an electronic apparatus, having a processor, a display and a data acquisition device, to execute the following steps:
displaying, by the processor on the display, a body shape image, wherein the body shape image matches a body dermatome distribution in response to the body shape image provided via the data acquisition device per a user request;
defining, by the processor, an affected part on the body shape image using the data acquisition device;
determining, by the processor, an area ratio according to an area of at least one dermatome covered by the affected part, wherein the determining comprises:
determining a center dermatome that is most covered by the affected part among the at least one dermatome;
setting the center dermatome and dermatomes of the body dermatome distribution that are adjacent to the center dermatome as a target region;
calculating an area of the center dermatome and the adjacent dermatomes;
calculating an area of dermatomes of the body dermatome distribution that are outside of the target region; and calculating the first area ratio as a ratio of the area of the center dermatome and the adjacent dermatomes to the area of the dermatomes that are outside of the target region;

determining, by the processor, whether the affected part concentrates on any one of a left side and a right side with respect to a center line of the body shape image and whether the calculated area ratio is smaller than a first predetermined ratio, wherein the first predetermined ratio is between 0.1 and 0.3;

deciding, by the processor, whether the defined affected part is herpes zoster according to a determination result; and treating the affected part in response to the defined affected part being decided to be the herpes zoster according to the determination results.

* * * * *